(12) United States Patent
Jawdosiuk et al.

(10) Patent No.: US 7,132,540 B1
(45) Date of Patent: Nov. 7, 2006

(54) HINDERED SPIRO-KETAL NITROXIDES

(75) Inventors: Mikolaj Jawdosiuk, Franklin, WI (US); George Sosnovsky, Milwaukee, WI (US); Jon Michael Clumpner, Sturgeon Bay, WI (US); Anthony J. O'Lenick, Jr., Dacula, GA (US)

(73) Assignee: Nova Molecular Technologies Inc., Janesville, WI (US)

( * ) Notice: Subject to any disclaimer, the term of this patent is extended or adjusted under 35 U.S.C. 154(b) by 291 days.

(21) Appl. No.: 10/949,562

(22) Filed: Sep. 27, 2004

Related U.S. Application Data

(63) Continuation-in-part of application No. 09/844,986, filed on Apr. 30, 2001, now abandoned.

(51) Int. Cl.
*C07D 491/113* (2006.01)
*C07D 491/10* (2006.01)

(52) U.S. Cl. .......................... 546/19; 546/16

(58) Field of Classification Search ............. 546/19, 546/16
See application file for complete search history.

(56) References Cited

U.S. PATENT DOCUMENTS 3,790,525 A * 2/1974 Murayama et al. ........... 524/99
4,124,564 A    11/1978 Minagawa et al.

* cited by examiner

*Primary Examiner*—Charanjit S. Aulakh

(57) ABSTRACT

The present invention discloses a series of novel hindered spiro-ketal nitroxides prepared by the ketalization reaction of 1,3-propanediols with triacetoneamine followed by oxidation. These novel spiro-ketals have unexpected advantages in hydrocarbon and monomer solubility which is important in styrene processing and refinery stream inhibition. Further, the invention shows an unexpected advantage over commercially available nitroxides in hydrocarbon solubility, especially in styrene and hydrocarbons. This invention also shows that these novel spiro-nitroxides are capable of inhibiting vinyl and acrylate polymerizations using an effective inhibition concentration of the nitroxide of the present invention.

9 Claims, No Drawings

HINDERED SPIRO-KETAL NITROXIDES

This application is a continuation in part of co-pending Ser. No. 09/844,986, filed Apr. 30, 2001.

FIELD OF THE INVENTION

The present invention relates to the composition of a series of novel hindered spiro-ketal nitroxides, prepared by the reaction of 1,3-propanediols with triacetoneamine to form ketal amines followed by oxidation of the ketal amine.

BACKGROUND OF THE INVENTION

Hindered nitroxides based on triacetoneamine, 4-oxo-2,2,6,6-tetramethylpiperidine have been known and two Nitroxides, 4-oxo TEMPO and 4-Hydroxy TEMPO have been used commercially for many years. These 4-substituted 1-oxyl-2,2,6,6-tetramethylpiperidines, generally produced in situ by oxidation of the parent amine, are used in polypropylene to prevent UV light degradation of the plastic. A good source of information of these uses is *Oxidation Inhibition in Organic Materials, Volume II* by Jan Pospisil and Peter P. Klemchuk, CRC Press, Inc., Boca Raton, Fla., 1990). When used in oxygen free atmospheres, the nitroxide itself is necessary to inhibit spurious free radical reactions. Consequently the pure nitroxyl compounds have been synthesized and offered commercially to inhibit polymerization of unsaturated hydrocarbon, styrene, vinyl and acrylic monomers during processing, distillation and storage. Hindered Nitroxides are also used as catalysts in selective oxidation of alcohols and experimentally for living polymerization.

4-Oxo-2,2,6,6-tetramethylpiperidine also known as 2,2,6,6-tetramethyl-4-piperidone or triacetoneamine, as produced commercially, is oxidized to produce 1-oxyl-4-oxo-2,2,6,6-tetramethylpiperidine, also known as 4-oxo TEMPO, a nitroxide with poor stability, even at ambient temperatures. This nitroxide has achieved limited use due to its poor stability even though its cost is low.

4-Hydroxy-2,2,6,6-tetramethylpiperidine is produced commercially by hydrogenation of 4-oxo 2,2,6,6-tetramethylpiperidine. 1-Oxyl-4-hydroxy-2,2,6,6-tetramethylpiperidine, also known as 4-Hydroxy TEMPO, is produced commercially by oxidation of 4-hydroxy-2,2,6,6-tetramethylpiperidine. It is used to prevent undesired free radical polymerization in styrene production and in refinery streams. This use is described in U.S. Pat. No. 5,254,760 and in Soviet Patent No. 1,558,888. A brief review of this subject is found in U.S. Pat. No. 6,117,276. Its use is limited because of its poor hydrocarbon solubility and poor stability in oxidizing media. In addition, the relationship of the vapor pressure vs. temperature described in the publication Hydrogenation of Alkenes and Alkynes Di-tert-alkyl Amines Di-tert-alkyl Nitroxyl (Aminoxyl) Radicals Polymerization Inhibitors G. Sosnovsky, M. Jawdosiuk, and J. M. Clumpner, *Zeitschrift für Naturforschung,* 55, 109 (2000) indicates a low volatility of this inhibitor, thus diminishing it role for potential use in the vapor phase.

2,2,6,6-Tetramethylpiperidine is made from 4-oxo-2,2,6,6-tetramethylpiperidine by the Wolff-Kishner reduction with hydrazine hydrate in ethylene or diethylene glycol. It is used to produce the nitroxide, 1-oxyl-2,2,6,6-tetramethylpiperidine, also known as TEMPO. It is used primarily to prevent undesired free radical polymerization. It is also used experimentally for living polymerization and for selective oxidation. While this nitroxide has good thermal stability, it has limited use because of the toxicity of the amine and its high cost.

2,2,6,6-Tetramethylpiperidine based spiro-ketal nitroxides have been mentioned in the literature but their physical properties have not been described there is no commercial supply available. A recent description of spiro-ketal nitroxyl radicals appeared in German Patent 42 19 471 A1 "N-Oxyl Derivatives of 2,2,6,6-Tetramethylpiperidine and Their Preparation" filed on Jun. 13, 1992. This patent relates to the preparation of nitroxyl radicals by catalytic oxidation of 2,2,6,6-tetramethylpiperidine ketals obtained from the following alcohols and glycols: methanol, ethanol, propanol, isobutanol, and n-butanol, ethylene glycol, 1,2-propanediol (propylene glycol), and 2,2-dimethyl-1,3-propanediol (neopentyl glycol). The latter three glycols, when reacted with 2,2,6,6-tetramethylpiperidine and then oxidized with hydrogen peroxide in the presence of catalytic amounts of divalent metals, such as magnesium or zinc, generate spiro-ketal nitroxides. The patent does not describe any physical properties or practical use of these nitroxyl radicals. U.S. Pat. No. 3,790,525 "4-Piperidone Ketal Derivatives, Their Preparation And Their Use As Stabilizers", filed Jan. 19, 1972 mentions a spiro-ketal nitroxide prepared from 1,3-propanediol and triacetoneamine, to form the ketal amine. No mention is made of the Nitroxide.

In U.S. Pat. No. 5,631,366 (May 20, 1997) 7,7,9,9-tetramethyl-1,4-dioxa-8-azaspiro[4.5]dec-8-yloxy, the spiro-ketal nitroxide derived from the reaction of ethylene glycol with 4-oxo-2,2,6,6-tetramethylpiperidine followed by oxidation, was used to convert an alcohol to an aldehyde is disclosed.

In JP 04362632 A2 (Dec. 15, 1992) photochromic materials containing 7,7,9,9-tetramethyl-1,4-dioxa-8-azaspiro[4.5]dec-8-yloxy or 2-(hydroxymethyl)-7,7,9,9-tetramethyl-1,4-dioxa-8-azaspiro[4.5]dec-8-yloxy spiro-ketal nitroxides were shown to have improved light resistance, transparency and evenness.

Yoshikawa and Negishi in JP 11286634 A2 (Oct. 19, 1999) have used 2-(hydroxymethyl)-7,7,9,9-tetramethyl-1,4-dioxa-8-azaspiro[4.5]dec-8-yloxy and similar spiro-ketal nitroxides, in thermosetting polymeric coating compositions of superior light stability.

The spiro-ketal nitroxides resulting from commercially available 1,3-propanediol and 2-methyl-1,3-propanediol were not mentioned in any of the above prior art.

We have now found that by oxidizing the ketals produced from 4-oxo-2,2,6,6-tetramethylpiperidine and 1,3-propanediol or 2-monosubstituted 1,3-propanediols with hydrogen peroxide, unique spiro-ketal nitroxides result. These unique spiro-ketal nitroxides have unique and useful properties displaying excellent (a) high-temperature stability, b) good volatility, (c) oxidative stability, (d) hydrophobic character (e) solubility in hydrocarbons and monomers and (f) inhibition of free radical reactions. They have unexpected advantages, when compared with commercially available nitroxides, in solubility in hydrocarbons and monomers, especially ethylbenzene and styrene. In addition, their high thermal stability and volatility makes it possible to use them in the vapor phase at elevated temperature employed in the commercial production of monomers. These are critical properties in the two major commercial use areas for nitroxides, styrene processing and refinery inhibitors.

The Invention

OBJECTIVE OF THE INVENTION

The object of this invention is to disclose new and unique spiro-ketal nitroxide compositions prepared from readily available 4-oxo-2,2,6,6-tetramethylpiperidine and 1,3-propanediols which have properties useful for the inhibition of polymerization of a variety of hydrocarbon, styrene, vinyl and acrylic monomers during processing, purification and storage.

SUMMARY OF THE INVENTION

The present invention relates to a series of novel hindered spiro-ketal nitroxides prepared by oxidation of the parent hindered spiro-ketal amines. These new and novel hindered spiro-ketal nitroxides have a unique combination of thermal stability, solubility and volatility properties. Another aspect of this invention is to demonstrate using these new and novel hindered spiro-ketal nitroxides as effective inhibitors of polymerization of unsaturated hydrocarbon, styrene, vinyl and acrylate monomers.

DETAILED DESCRIPTION OF THE INVENTION

The compounds of the present invention are spiro-ketal nitroxide compounds and as such are unique in structure and function as free radical scavengers. These compounds display excellent (a) high-temperature stability, (b) high volatility, (c) oxidative stability, (d) hydrophobic behavior, (e) solubility in hydrocarbons and monomers and (f) inhibition of free radical reactions. Additionally, they have unexpected advantages in solubility in hydrocarbons and monomers, a critical property in styrene processing and refinery inhibitors.

The compounds of the present invention conform to the following structure:

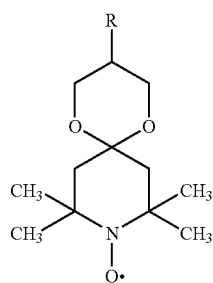

wherein;

R is selected from the group consisting of hydrogen, methyl, ethyl, n-propyl, iso-propyl, n-butyl, 1-methylpropyl and iso-butyl.

Preferred Embodiments

In the first set of preferred embodiments the compounds of the present invention conform to the following structure;

wherein;

R is selected from the group consisting of hydrogen and methyl.

EXAMPLES

Procedure

The hindered spiro-ketal amine used in these examples was prepared by a classical ketalization reaction exemplified in U.S. Pat. No. 3,790,525, "4-Piperidone Ketal Derivatives, Their Preparation and Their Use as Stabilizers". The raw materials used to make 1,5-dioxa-9-aza-8,8,10,10-tetramethylspiro[5,5]undecane, the spiro-ketal amine, were 4-oxo-2,2,6,6-tetramethylpiperidine and 1,3-propanediol.

Preparation of Spiro-ketal Nitroxides

Example 1

Preparation of 1,5-dioxa-9-aza-8,8,10,10-tetramethylspiro[5,5]undec-9-yloxy 1,5-Dioxa-9-aza-8,8,10,10-tetramethylspiro[5,5]undecane was subjected to oxidation with hydrogen peroxide in the presence of sodium tungstate. The initial oxidation was carried out in methanol in a standard fashion.

1,5-Dioxa-9-aza-8,8,10,10-tetramethylspiro[5,5]undecane (8 g, 0.04 mole) was dissolved in 150 ml of methanol in a 500 ml Erlenmeyer flask. To the resulting light brown solution 40 ml of 35% aqueous hydrogen peroxide was added in one portion followed by 0.4 g of sodium tungstate dihydrate. The mixture was left for 3 days at room temperature (about 25° C.). After one day the color changed to dark orange. No noticeable exotherm was observed. After 3 days the mixture was transferred to a 1-liter separatory funnel, diluted with 500 ml of water and extracted with three 50 ml portions of t-butyl methyl ether (MTBE). The extract was dried with anhydrous sodium sulfate, filtered and evaporated on a rotary evaporator to give a dark orange liquid, which quickly solidified to a dark orange solid product with m.p. 59–62° C. Yield 9 g.

Example 2

Preparation of 1,5-dioxa-9-aza-8,8,10,10 tetramethylspiro[5,5]undec-9-yloxy

Distilled ketal amine, 1,5-dioxa-9-aza-8,8,10,10-tetramethylspiro[5,5]undecane (21.3 g, 0.1 mole) was dissolved in 120 ml of methanol. To this solution 50 ml of 35% aqueous hydrogen peroxide was added in one portion followed by 0.4 g of sodium tungstate hydrate. The solution was left at room temperature for 3 days at room temperature (about 25° C.). The mixture was worked up in the same fashion as described in Example 1. Three extractions with 50 ml of MTBE afforded 19 g of the product. Two additional extractions with 50 ml produced an additional 4 g of the same product. Total yield 23 g. M.p. 59–70° C.

The product (17 g) was stirred with toluene (70 ml, 59 g). About one half of the material dissolved rapidly to form a dark orange solution. Another half was left as large solid yellow needles with m.p. 80–83° C. The yellow solid was filtered off and air dried (9 g). The toluene soluble material was evaporated to give 8 g of an orange solid with m.p. 52–65° C.

Both solids (yellow and orange) were analyzed by mass spectroscopy (chemical ionization). The resulting spectra were identical—consistent with the expected 1,5-dioxa-9-aza-8,8,10,10-tetramethylspiro[5,5]undec-9-yloxy. Both spectra contained the molecular ion M+1 at 229, M at 228 and M+1-CH3 at 214.

Inhibition Properties:

Testing was done to determine the effectiveness of various nitroxides in inhibiting the polymerization of various vinyl monomers. Many of the nitroxyl radicals tested exhibited high thermal stability, however, the solubility of some of them in common monomers is low.

General Procedure.

A sample of vinyl monomer (10 ml) was placed in an open 25 ml test tube. To each tube benzoyl peroxide (0.35 g) and 0.1 g of nitroxide inhibitor was added, then the tubes were placed in a water bath maintained by a thermostat at 70° C. The selected vinyl monomers polymerize under these conditions without nitroxide inhibitors within a few minutes.

Vinyl monomers: acrylonitrile, vinyl acetate and methyl acrylate.

Inhibitors (made using the procedures above):

| Example | Description |
|---|---|
| 1 | 1-oxyl-4-acetamido-2,2,6,6-tetramethylpiperidine |
| 2 | 1-oxyl-4-benzoyloxy-2,2,6,6-piperidine |
| 3 | 1-oxyl-4-methoxy-2,2,6,6-tetramethylpiperidine |
| 4 | 1,5-dioxa-9-aza-8,8,10,10-tetramethylspiro[5,5]undec-9-yloxy |
| 5 | 1-oxyl-2,2,6,6-tetramethylpiperidine |
| 6 | N-oxyl-di-t-butylamine |

Polymerization of Acrylonitrile at 70° C. in the presence of Nitroxide Inhibitors.

| Inhibitor | Quantity | Inhibition Time |
|---|---|---|
| none | 0.0 g | 4 min |
| 1 | 0.1 g | 40 min |
| 2 | 0.1 g | 60 min |
| 3 | 0.1 g | 305 min |
| 4 | 0.1 g | 135 min |
| 5 | 0.1 g | 60 min |
| 6 | 0.1 ml | 180 min |

Polymerization of Vinyl Acetate at 70° C. in the presence of Nitroxide Inhibitors.

| Inhibitor | Quantity | Inhibition Time |
|---|---|---|
| none | 0.0 g | 8 min |
| 1 | 0.1 g | 205 min |
| 2 | 0.1 g | 145 min |
| 3 | 0.1 g | >300 min |
| 4 | 0.1 g | 250 min |
| 5 | 0.1 g | 385 min |
| 6 | 0.1 ml | 130 min |

Polymerization of Methyl Acrylate at 70° C. in the presence of Nitroxide Inhibitors.

| Inhibitor | Quantity | Inhibition Time |
|---|---|---|
| none | 0.0 g | 10 min |
| 1 | 0.1 g | 165 min |
| 2 | 0.1 g | 166 min |
| 3 | 0.1 g | >300 min |
| 4 | 0.1 g | 110 min |
| 5 | 0.1 g | 180 min |
| 6 | 0.1 ml | 320 min |

These results indicate that the inhibitor of Example 4, the hindered spiro-ketal nitroxide, performed well in the tests. The presence of any of the nitroxide inhibitors allows one to stop the polymerization process for several hours. Note that polymerization takes place in 10 minutes or less when no inhibitor is present.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A compound conforming to the following structure:

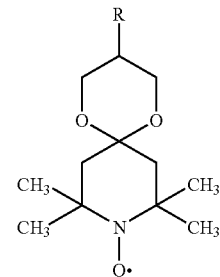

wherein;
R is selected from the group consisting of hydrogen, methyl, ethyl and n-propyl,
isopropyl, n-butyl, isobutyl, and 1-methylpropyl.

2. A compound of claim 1 wherein R is hydrogen.
3. A compound of claim 1 wherein R is methyl.
4. A compound of claim 1 wherein R is ethyl.
5. A compound of claim 1 wherein R is n-propyl.
6. A compound of claim 1 wherein R is isopropyl.
7. A compound of claim 1 wherein R is n butyl.
8. A compound of claim 1 wherein R is isobutyl.
9. A compound of claim 1 wherein R is 1-methylpropyl.

* * * * *